United States Patent
Cheal et al.

(10) Patent No.: US 7,572,297 B2
(45) Date of Patent: *Aug. 11, 2009

(54) TAPERED JOINT PROSTHESIS

(75) Inventors: Edward J. Cheal, Duxbury, MA (US); George B. Cipolletti, Duxbury, MA (US)

(73) Assignee: OMNI life science, Inc., Raynham, MA (US)

( * ) Notice: Subject to any disclaimer, the term of this patent is extended or adjusted under 35 U.S.C. 154(b) by 37 days.

This patent is subject to a terminal disclaimer.

(21) Appl. No.: 10/595,291

(22) PCT Filed: Oct. 8, 2004

(86) PCT No.: PCT/US2004/033385

§ 371 (c)(1), (2), (4) Date: Apr. 5, 2006

(87) PCT Pub. No.: WO2005/034817

PCT Pub. Date: Apr. 21, 2005

(65) Prior Publication Data

US 2007/0043447 A1   Feb. 22, 2007

Related U.S. Application Data

(60) Provisional application No. 60/509,528, filed on Oct. 9, 2003.

(51) Int. Cl.
*A61F 2/32* (2006.01)
(52) U.S. Cl. .................................. 623/22.43
(58) Field of Classification Search .... 623/21.11–23.39
See application file for complete search history.

(56) References Cited

U.S. PATENT DOCUMENTS

| | | | |
|---|---|---|---|
| 3,846,846 A | 11/1974 | Fischer | |
| 4,051,559 A | 10/1977 | Pifferi | |
| 4,212,087 A | 7/1980 | Mortensen | |
| 4,520,511 A | 6/1985 | Gianezio et al. | |
| 4,608,055 A * | 8/1986 | Morrey et al. | 623/22.46 |
| 4,624,673 A | 11/1986 | Meyer | |
| 4,676,797 A | 6/1987 | Anapliotis et al. | |
| 4,693,724 A | 9/1987 | Rhenter et al. | |
| 4,790,852 A | 12/1988 | Noiles | |
| 4,846,839 A | 7/1989 | Noiles | |
| 4,851,007 A | 7/1989 | Gray | |
| 4,908,032 A * | 3/1990 | Keller | 623/23.45 |
| 4,963,155 A * | 10/1990 | Lazzeri et al. | 623/22.42 |
| 4,995,883 A | 2/1991 | Demane et al. | |

(Continued)

FOREIGN PATENT DOCUMENTS

EP    0562782    9/1993

(Continued)

*Primary Examiner*—David J Isabella
*Assistant Examiner*—Ann Schillinger
(74) *Attorney, Agent, or Firm*—Scott E. Kamholz; Foley Hoag LLP

(57) ABSTRACT

A joint prosthesis may include a modular head member, a modular body member, and a stem member. The stem member may be so tapered as to be engageable by taper press-fit into the medullary cavity of a bone. The body member may be engageable in the stem member by friction-tight press-fit at a zone of diametrical interference.

30 Claims, 7 Drawing Sheets

U.S. PATENT DOCUMENTS

| | | | |
|---|---|---|---|
| 5,002,578 A | 3/1991 | Luman | |
| 5,002,581 A | 3/1991 | Paxson et al. | |
| 5,030,234 A | 7/1991 | Pappas et al. | |
| 5,032,130 A * | 7/1991 | Schelhas et al. | 623/22.42 |
| 5,035,712 A | 7/1991 | Hoffman | |
| 5,035,717 A | 7/1991 | Brooks | |
| 5,047,033 A | 9/1991 | Fallin | |
| 5,074,060 A * | 12/1991 | Brncick et al. | 36/77 R |
| 5,074,879 A | 12/1991 | Pappas et al. | |
| 5,080,685 A | 1/1992 | Bolesky et al. | |
| 5,108,437 A | 4/1992 | Kenna | |
| 5,108,452 A | 4/1992 | DeMane et al. | |
| 5,135,529 A | 8/1992 | Paxson et al. | |
| 5,163,961 A | 11/1992 | Harwin | |
| 5,181,928 A | 1/1993 | Bolesky et al. | |
| 5,201,882 A | 4/1993 | Paxson | |
| 5,286,260 A | 2/1994 | Bolesky et al. | |
| 5,342,366 A | 8/1994 | Whiteside et al. | |
| 5,370,706 A | 12/1994 | Bolesky et al. | |
| 5,405,394 A | 4/1995 | Davidson | |
| 5,507,824 A | 4/1996 | Lennox | |
| 5,507,830 A * | 4/1996 | DeMane et al. | 623/22.42 |
| 5,549,706 A | 8/1996 | McCarthy | |
| 5,601,567 A | 2/1997 | Swajger et al. | |
| 5,653,764 A | 8/1997 | Murphy | |
| 5,653,765 A * | 8/1997 | McTighe et al. | 623/22.42 |
| 5,658,349 A | 8/1997 | Brooks et al. | |
| 5,702,480 A | 12/1997 | Kropf et al. | |
| 5,876,459 A | 3/1999 | Powell | |
| 5,888,245 A | 3/1999 | Meulink et al. | |
| 5,902,340 A * | 5/1999 | White et al. | 128/898 |
| 6,264,699 B1 | 7/2001 | Noiles et al. | |
| 6,299,648 B1 * | 10/2001 | Doubler et al. | 623/23.18 |
| 6,319,286 B1 | 11/2001 | Fernandez et al. | |
| 6,702,854 B1 | 3/2004 | Cheal et al. | |
| 6,706,072 B2 * | 3/2004 | Dwyer et al. | 623/22.42 |
| 7,044,975 B2 * | 5/2006 | Cheal et al. | 623/22.42 |

FOREIGN PATENT DOCUMENTS

| | | |
|---|---|---|
| EP | 0567349 | 10/1993 |
| EP | 0592897 | 4/1994 |
| EP | 0433121 | 6/1994 |
| EP | 0679375 | 9/1998 |
| EP | 0612509 | 7/1999 |
| WO | WO 93/02641 | 2/1993 |
| WO | WO 96/00539 | 1/1996 |
| WO | WO 00-72784 A1 | 12/2000 |

* cited by examiner

Section through mid shaft (10)

Section through distal shaft (9)

Section through distal shaft (9)

Section through distal shaft (9)

Section through distal shaft (9)

TAPERED JOINT PROSTHESIS

CROSS-REFERENCE TO RELATED APPLICATION

This application claims the benefit of U.S. Provisional Pat. App. Ser. No. 60/509,528, filed Oct. 9, 2003, hereby incorporated herein by reference.

BACKGROUND

Artificial hip joint prostheses are widely used today, restoring mobility to patients affected by a variety of conditions, particularly arthritis. The satisfactory performance of these devices can be affected not only by the design of the component itself but also by the final placement and geometry of the implanted component and by the long-term fixation of the device. Improper placement or positioning of the device or an improper fit to the patient's anatomy can adversely affect the goal of satisfactorily restoring the clinical biomechanics and function of the joint.

The primary role of the artificial hip prosthesis is to restore the diseased and/or damaged joint to normal function. This function causes significant forces such as axial, bending, and rotational forces, to be imparted to the device. The component must remain adequately fixed within the medullary canal while it endures these forces, because adequate fixation of the component is necessary to ensure proper functioning and a long useful life of the artificial hip component. Early designs of artificial hip components relied primarily on cemented fixation. These cements, such as polymethylmethacrylate, were used to anchor the component within the medullary canal by acting as a grouting agent between the component and the endosteal (inner) surface of the bone. While this method of fixation by cement provides immediate fixation and resistance to the forces encountered and allows the surgeon to position the device effectively before the cement sets, it is not without problems. Over time the mechanical properties and the adhesive properties of the bone cement degrade; eventually the forces overcome the cement and cause the components to become loose due to a failure at the cement/bone or cement/stem interface.

Alternative approaches to address the issue of cement failure include both biological ingrowth and press-fit stems, separately and in combination. Stems designed for biological ingrowth typically rely on the bone itself to grow into a specially prepared surface of the component. The approach firmly anchors the device within the medullary canal, but it does not result in immediate fixation of the component because it takes time for the bone to grow into the specially prepared surface. Press-fit stems may or may not have specially prepared surfaces and typically rely on some degree of interference fit of the component within the bone's medullary canal to achieve stable fixation. One particular type of press-fit stem is tapered in one or more planes such that the degree of press-fit of the stem into the medullary canal increases as the stem is more deeply seated into canal. While a tapered stem design has the advantage of reliably producing a stable press-fit condition in the bone, provided the stem is properly sized for the particular bone, the final position of the stem will depend on a number of variables, including bone geometry, bone quality, stem geometry, and surgical technique.

The hip head center of rotation is determined by the head position because typical hip heads are spherical. In most devices the head position is determined by the stem position because the two are connected through an integral neck. Many devices in existence use modular hip heads to increase or decrease neck length, which alters both head height and head offset proportionately and simultaneously. The neck portion of the device that is attached to the stem receives the modular heads. This results in the head position being integrally linked and thus aligned with and determined by, the stem portion. Multiple positions of the heads are accomplished by using hip heads with various bore dimensions and extended or reduced offsets or skirts which limit the positioning of the head to the angled neck axis. In many instances this may not be appropriate as one may only wish to increase offset while maintaining head height (or vice versa), which can not be accomplished with the modular head type devices previously described. In addition, one could not address anteversion of the neck in such a device as described. The amount of anteversion is determined by the angular difference between the stem-axis/neck-axis plane to that of the coronal plane. Since the head position is directly linked to the stem position, anteversion can only be achieved by sacrificing stem position by rotating the stem.

Some devices incorporate modular components, such as modular stems with modular sleeves, or modular proximal and distal portions of the stem, to provide some degree of adjustability for the final stem geometry. This adjustability may or may not include lateral offset, leg length, and/or anteversion, depending on the specifics of the design and on the available component. Such devices have two basic means of connection, tapers and threads, used alone or in combination. Taper connections have the disadvantage that the final axial position of the two components, relative to each other, is dependent on the precise geometry of the tapers; deviations in geometry within the tolerances allowed for manufacturing results in deviations in the final axial position of the modular component with the tapered connection. The strength of the coupling between the components with the tapered connection is also in part dependent on the level of force used to assemble the components. Similarly, threaded connections have the disadvantage that the strength of connection is in part dependent on the magnitude of torsion applied to the threaded coupling mechanism during assembly. Insufficient impaction force for tapered connections, and/or insufficient torsion for threaded connections, applied during assembly can leave the assembled component at risk of disassembly during the functional lifetime of the device. Unintended disassembly of implanted components is a serious complication that generally requires medical intervention ranging in severity from closed manipulation to surgical revision. This can be a significant risk for tapered and/or threaded coupling means especially considering that the assembly is accomplished in the operating room, rather than under more controlled conditions such as in a factory, in order to take full advantage of the modularity. Thus a design that provides a coupling means for the modular components that has a more reproducible final geometry and reproducible strength of connection, that is less dependent on the surgeon, operating room staff, or other persons acting outside the place of manufacture, would be of significant benefit.

SUMMARY

The disclosed components permit superior sizing and positioning of joint prosthesis components. In one embodiment, a joint prosthesis includes a modular head member, a modular body member, and a stem member. The stem member is so tapered as to be engageable by taper press-fit into the medullary cavity of a bone. The body member is engageable in the stem member by friction-tight press-fit at a zone of diametrical interference.

DETAILED DESCRIPTION

Figure 1:
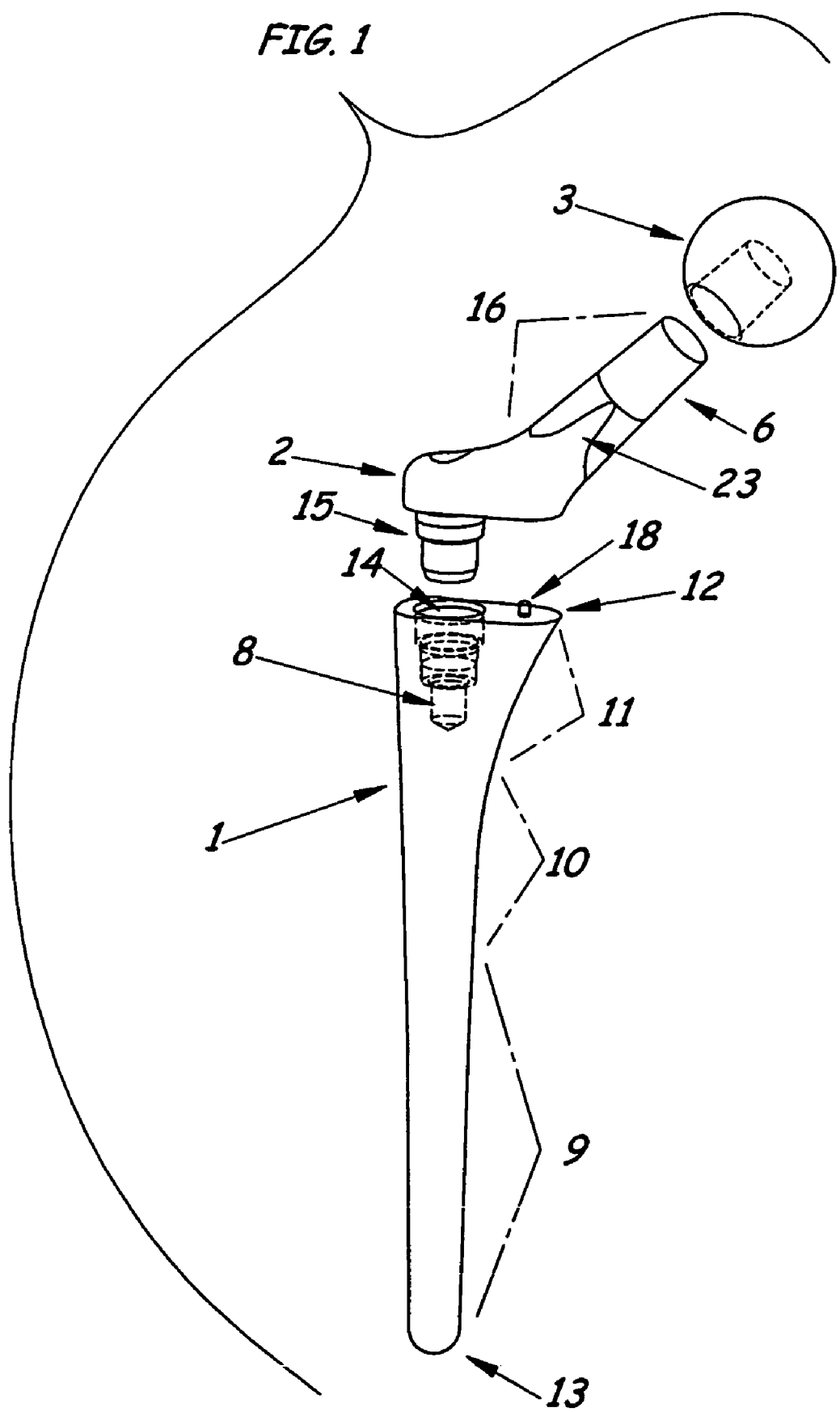
FIG. 1 is an exploded view of an exemplary embodiment of a joint prosthesis.

The present subject matter is particularly described with reference to the femoral component of an artificial hip prosthesis for both cemented and cementless applications; however, the disclosed devices are also applicable to other implantable prostheses, such as knees, elbows, and shoulders, all of which may include a stemmed portion for insertion into a bone cavity. The present subject matter is particularly advantageous in allowing optimal placement and secure attachment for use in an artificial hip, so this description will reference a hip prosthesis.

The positioning of the prosthetic device, including the location of the head center relative to the medullary stem, affects the biomechanics of the joint. Better positioning results in a more efficient joint and thus lower forces on the device. The disclosed components can de-couple the stem's positioning from the final positioning of the head center, to allow for both optimal positioning and secure engagement to be achieved independently of each other.

The combination of a tapered stem with a modular body can provide special advantages: the tapered stem permits secure seating in bone, while body modularity permits fine control of overall prosthesis length. The tapered stem component can be seated in a medullary canal by taper press-fitting. The quality of the taper press-fit depends on how deeply the stem is pushed into the canal and on how much force is used to push it. As a result, there is considerable variability in the stem component depth which cannot be predicted easily before implantation. This variability can aggravate leg-length problems (i.e., the length of an extremity receiving the prosthesis will depend on the depth of stem seating). This problem can be lessened by providing a modular body member to be connected to the stem component. Because the body member is modular, a range of sizes can be provided so that the appropriate size can be selected to achieve the best overall size of the prosthesis. This, in turn, reduces leg length variability. The best-sized body member can be selected on a case-specific basis to compensate for the seating-depth variability of the tapered stem.

The disclosed components can allow for neck geometry and rotational neck positioning that are independent of the engagement/positioning of the stem after full insertion of the stem is achieved. As a result, they can achieve variable positioning of the hip center of rotation independent of stem position as well as independent of both head offset and head height. In addition, they can also facilitate stem placement independent of neck axis placement to achieve the desired anteversion.

Different and distinct modular proximal bodies can be used to result in differing ratios of head offset to head height when combined with selected modular hip heads. One can also accommodate a degree of unpredictability in placement and seating of the stem by selection of the proximal body after insertion of the stem into the medullary canal. Separate proximal portions have the additional benefit of being able to address anteversion of the head position independent of stem placement. Assembly of the components can be accomplished either before implantation, such as on the back table during surgery, or, alternatively the assembly can be accomplished in a successive fashion, assembling each portion independently during implantation to maximize the benefits of independent positioning of the individual sub-components of the device within the bone.

The cylindrical press-fit coupling between the proximal body and the stem of some embodiments provides a reproducible strength and geometry of assembly between the two portions; this coupling means only requires axial translation of the proximal body into the stem, where full assembly is defined by seating of the proximal body to the stem, which could not be achieved with the use of a tapered coupling means. Provided the two portions are fully assembled, the resulting strength of assembly and the axial position of the proximal body relative to the stem are dependent on the design and manufacturing tolerances, and are not dependent on the magnitude of force applied during assembly, unlike tapered and/or threaded coupling means.

The stem and proximal bodies can be de-coupled by providing them as two distinct pieces. The modular proximal body may be combined with the modular stem to allow additional rotational alignment and positioning of the proximal body independent from and relative to the stem. This achieves additional variable positioning independent of that achieved after insertion of the stem. In some embodiments, the modular proximal body can be locked to the stem in one of several positions to achieve the desired amount of rotational alignment. By varying proximal body configurations a variety of clinical needs and situations can be addressed such as calcar replacement type devices or satisfying the need of extremely offset necks without requiring a whole new stem system. Many more clinical situations can be addressed by simply using the appropriate proximal body configuration designed for that purpose.

The stem utilizes a tapered external geometry for interfacing with the recipient bone such that a press-fit of the stem is achieved as the stem is inserted into the prepared medullary canal. Prior to stem insertion, the canal can be prepared using one or more reamers, broaches, rasps, or similar instruments to create the appropriate cavity in the recipient bone. After preparation of the bone, the stem is forcibly inserted into the prepared cavity until the proper rotational position and sufficient insertion depth and press-fit stabilization are achieved. Through the availability of a selection of proximal bodies with various geometries and rotational positions, various stem positions after insertion can be accommodated while still achieving the proper final geometry of the implant assembly.

Additional positioning options exist with the addition of modular heads that are assembled to one of the several proximal bodies envisioned to achieve independent head offset and head height options. Due to the extent of options available, and the desire for a system approach in addressing a multitude of clinical situations with limited components, connection means between the components is simplified and common amongst the components resulting in a reliable, more cost effective, and user friendly means to secure the components either prior to, immediately prior to, or during implantation.

Figure 2:
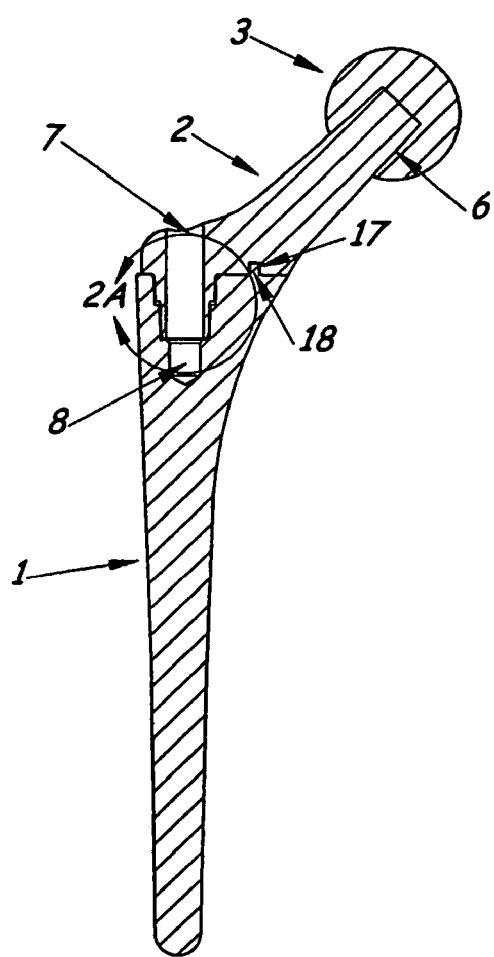
FIG. 2 is a longitudinal cross section view of an assembled joint prosthesis.

As shown in FIGS. 1-2, the illustrated embodiment includes an elongated stem 1 which is to be inserted into the medullary canal of the bone. The stem extends from proximal portion 12 to distal tip 13. The stem 1 is joined to a separate proximal body 2 by various attachment/locking mechanisms shown in FIG. 2. A modular hip head 3 can be attached to the neck 16 of the proximal body to complete the device. The assembly of the device is not limited temporally; assembly can occur before surgery, immediately prior to implantation, or during implantation. The attachment mechanisms described below allow for ease of assembly with limited access.

The distal portion 9 of the stem can have a variety of cross-sectional shapes, such as circular, rounded, elliptical, or rectangular, or some combination of these shapes. The stem is so tapered such that its cross-sectional area decreases from its proximal end to its distal end. The taper may be continuous; that is, it may taper smoothly to facilitate engagement of the tapered surface in a medullary cavity.

The taper, in some embodiments, may be confined to one or more portions of the stem, such as the proximal portion 11, the mid shaft portion 10, and the distal portion 9. The taper may be in the medial-lateral dimension only, or may be in both the medial-lateral dimension and the anterior-posterior dimension. The distal 9, mid shaft 10, and/or proximal portions 11 may include grooves, slots, or longitudinal ridges with intervening flutes to aid in positioning of the stem and to provide increased rotational stability of the stem in the bone. These grooves, slots, ridges, and/or flutes may extend to or near the distal end of stem or may be limited to the mid shaft portion of the stem. The mid shaft portion 10 blends into the relatively larger proximal portion 11 of the stem. The proximal portion tends to match the bone-canal contour, which is larger on the medial side of the device.

Located on the proximal end 12 of the stem is a bore 14 which may be aligned with or oriented at an angle to the longitudinal stem axis. The bore 14 may be cylindrical. The bore 14 may include a blind hole 8 at its base. This hole may include threads or other features for engaging a screw, bolt, or rod, thereby removably secured to the stem 1. Such screw, bolt, or rod, may be used as part of an assembly device to secure the stem and proximal body together by simultaneously applying appropriate forces to the stem and body. The hole 8 may also serve as a purchase for an instrument to remove the prosthesis from the bone in which it is implanted.

In some embodiments, the proximal surface of the stem 12 may include a key, tab, or pin 18 for rotational alignment of the proximal body. This alignment feature 18 may also contribute to the torsional strength of the modular junction.

An inventory would typically be kept of hip prosthesis stems ranging in size from 8 to 20 mm (measured in the medial-lateral dimension and taken at about the transition from distal stem 9 to mid shaft 10; in the case on a round stem, the dimension is the diameter); this range is suitable for most of the population. Patients requiring sizes smaller or larger, although uncommon, would typically be accommodated through custom devices.

Figure 3:
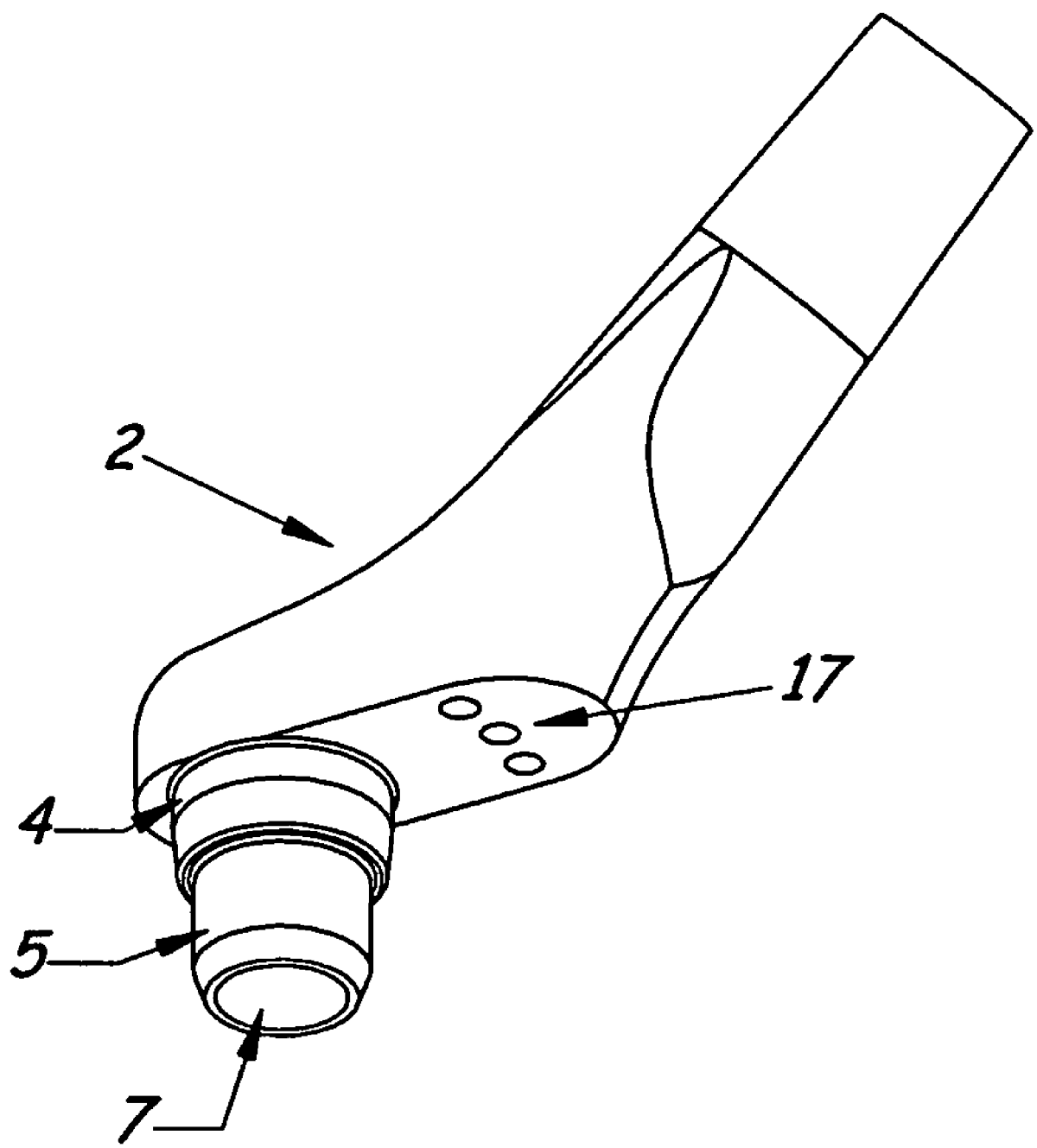
FIG. 3 is a view of a proximal body of a joint prosthesis.

The proximal body 2, also shown in FIG. 3, is initially separate from the stem 1 and typically joined to the stem by the implanting surgeon or assistant. This modularity gives the user additional flexibility in final stem placement. De-coupling stem placement from proximal body placement affords substantially more flexibility and provides the ability to address anteversion. Optimal positioning can be achieved by choosing the appropriate proximal body to use with the chosen stem. For instance, for a given stem, choosing among nine unique proximal bodies and modular heads having four different offsets gives the surgeon the choice of thirty-six lateral offset/leg length positions.

In addition, each of these thirty-six positions can be further adjusted by rotation of the proximal body with respect to the stem prior to final seating of the proximal body, resulting in the desired combination of anteversion, lateral offset, and leg length. Primary positioning is obtained by indexing the keyed portion 18 of the stem 1 to that of the receiving slot or holes 17 of the proximal body 2. The number of receiving holes may vary. Three to six discrete positions provide enough variation for most applications, although there could be as few as one (for simply locking) or two receiving holes. More than twelve positions, while theoretically possible, are probably unnecessary.

The neck 16 (FIG. 1) of the proximal body 2 is attached to or integral with the body's base and projects outwardly from it, at an angle typically in the range of about 40° to about 50° relative to the long axis of the stem. In one embodiment, the neck projects at 45°. The cross-sectional geometry of the neck is typically round. Flat cutouts (23) on the neck may be incorporated to maximize the range of motion before impingement of the neck occurs on the surrounding bone (such as the acetabulum in the case of a hip joint prosthesis). One end of the neck is blended into the base of the proximal body while the opposite end forms a plug 6, such as the depicted conical tapered plug. The plug receives a modular head 3 that has a corresponding bore, such as the tapered bore in the depicted modular hip head. The head can be secured on the neck plug by a wide variety of mechanisms, such as cement, press fit, and/or mating screw threads. The modular heads 3 are sized and shaped such that they fit into a corresponding receiver component (not shown), such as an acetabular cup component in the case of a hip prosthesis. Existing metal or ceramic heads commonly used in implantable prostheses can be used as modular heads as long as they have or are provided with a suitable corresponding bore that mates with the plug at the end of the neck.

In some embodiments, the proximal body 2 may include a bore hole 7 (FIG. 2) through the spigot 15. This bore hole may include threads or other features for removably engaging a bolt, rod, or plug. The bolt or rod could be included for a variety of uses, such as removing the neck from the stem, or removing the assembled construct from the bone. The plug could be used to close the hole and keep the internal surfaces clean. The bore hole could also be used to enable a rod to pass through the proximal body, the rod removably engaging the stem 1 at the stem bore hole 8, as part of a device to forcibly assemble the proximal body into the stem.

As discussed above, the modularity of the proximal body 2 permits the use of a variety of neck configurations 16 with the same stem 1. Proximal bodies can be varied, for example, in neck angles and neck lengths, thereby creating flexibility in overall prosthesis length and head positioning. When modular heads 3 are attached to these varying proximal bodies, the configuration options multiply significantly with very little increase in number of individual sub-components such as modular heads and proximal bodies.

The stem 1, proximal body 2, and head portions 3 of a prosthesis can be fabricated from a wide variety of biocompatible materials. Suitable examples include titanium alloys, cobalt alloys, and stainless steel alloys. In certain embodiments, Ti-6Al-4V can be used for stem and/or proximal bodies. In certain embodiments, Co—Cr alloys can be used for a head portion.

Final locking of the proximal body 2 to the stem 1 is obtained by press-fitting a male spigot 15 of the proximal body 2 within a corresponding bore 14 of the stem. The length of the spigot is not critical; it should be long enough to provide a suitable locking surface and adequate axial engagement. For example, a length of about 0.8" (about 20 millimeters) can be satisfactory for the femoral component of a hip replacement.

Figure 2A:
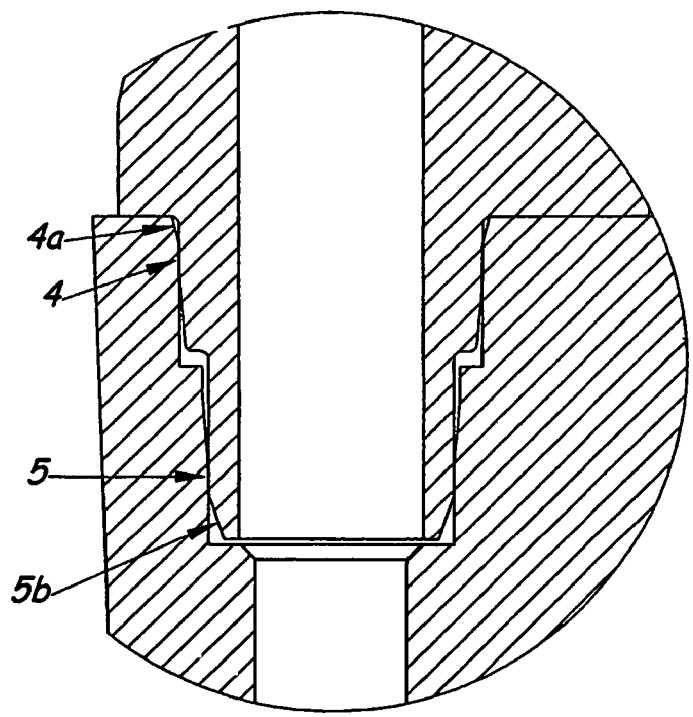
FIG. 2A shows detail from FIG. 2.

The locking is achieved by one or more zones of diametrical interference between the spigot and bore. FIG. 2A shows detail of FIG. 2 and depicts one embodiment of a locking system that includes two zones of diametrical interference 4 and 5. The zones of diametrical interference on the spigot (termed "locking bands") and their corresponding zones of diametrical interference in the bore (termed "receiving portions") are geometrically similar (i.e. have the same or substantially the same shape). In the depicted embodiment, each zone is cylindrical (i.e., circular cross-section of uniform geometry transverse to the spigot's axis), but a locking band and its corresponding receiving portion may be otherwise so shaped as to have uniform cross-sectional geometries along their lengths. To obtain the interference fit between the spigot and bore at zones 4 and 5, the outer dimensions of the spigot should exceed the inner dimension of the bore. For example, when the zones are cylindrical, each of the spigot's zones' outer diameters should exceed the inner diameters of the corresponding zones of the bore. When the zones have other shapes, the dimensions of the spigot zones should exceed the respective dimensions of the bore. The dimensional difference between the spigot and the bore may be in the range of about 0.0005" to about 0.0035" (about 10 microns to about 100 microns). The two zones need not have equal dimensional differences. For example, in one embodiment, zone 4 can have a dimensional difference of about 0.0020" (about 50 microns) and zone 5 can have a dimensional difference of about 0.0010" (about 25 microns). The length of a zone of diametrical interference (that is, its extent along the spigot's axis) may be varied in relation to the amount of rotational resistance desired. In some embodiments, each zone length can be in the range of about 0.020" to about 0.080" (about 0.5 millimeters to about 2.0 millimeters) to provide enough interfering surface area to ensure adequate rotational resistance of the proximal body within the stem, while maintaining reasonable assembly forces by controlling the amount of interference, the length of the zone and the axial location of the zone(s).

One or both of the spigot and bore can incorporate tapers and/or rounds at the surfaces leading into the zones of diametrical interference so as to avoid plowing of one or more surfaces during assembly, and thus ease assembly of the proximal body to the stem. In the embodiment depicted in FIG. 2A, the spigot has a taper 5b and the bore has a taper 4a.

Figure 4:
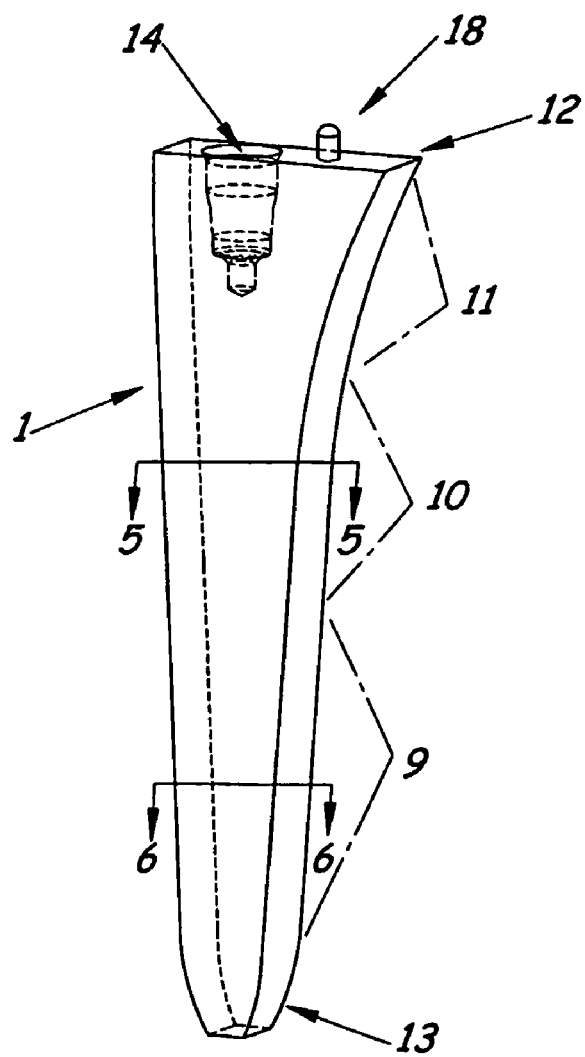
FIG. 4 is a view of a stem component of another exemplary embodiment of a joint prosthesis.
Figure 5:
FIG. 5 is a cross section taken at the line 5-5 in FIG. 4.
Figure 6:
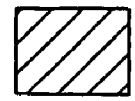
FIG. 6 is a cross section taken at the line 6-6 in FIG. 4.
Figure 7:
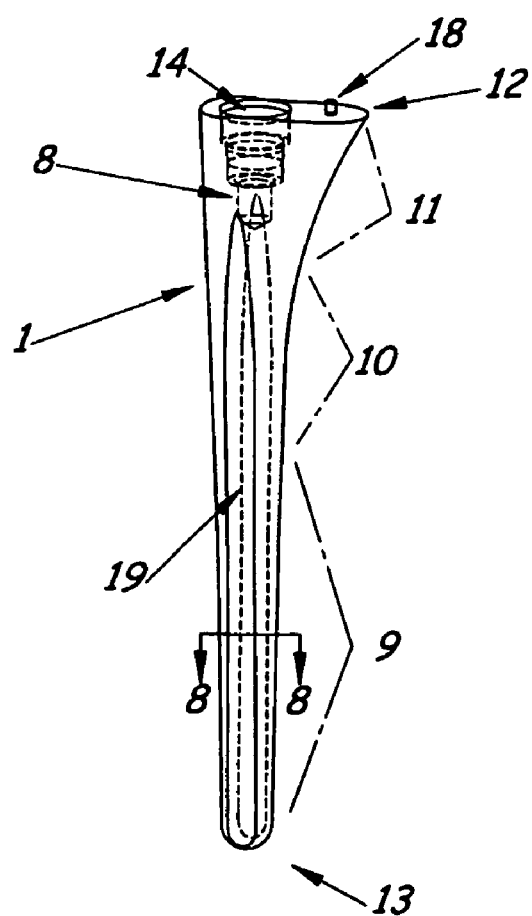
FIG. 7 is a view of a stem component of another exemplary embodiment of a joint prosthesis.
Figure 8:
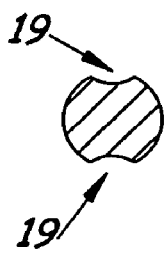
FIG. 8 is a cross section taken at the line 8-8 in FIG. 7.
Figure 9:
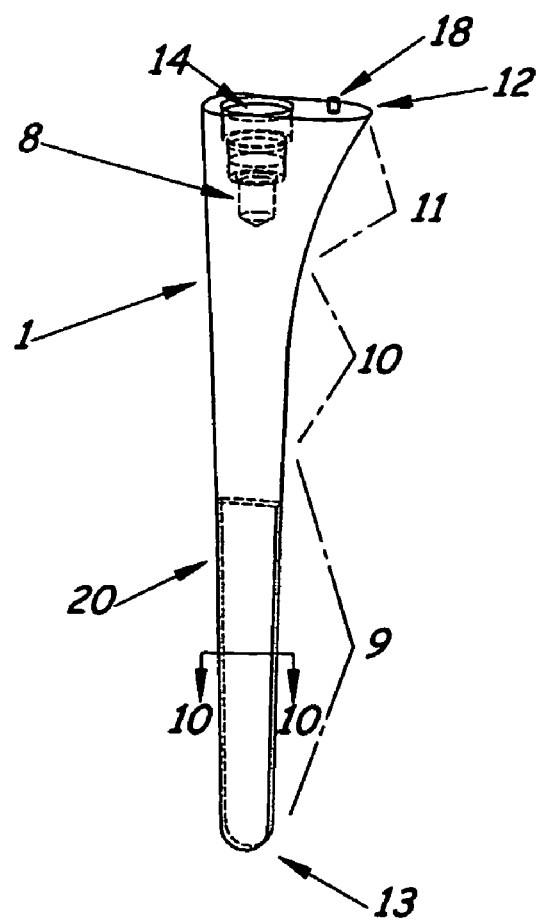
FIG. 9 is a view of a stem component of another exemplary embodiment of a joint prosthesis.
Figure 10:
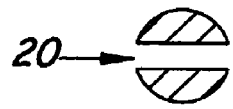
FIG. 10 is a cross section taken at the line 10-10 in FIG. 9.
Figure 11:
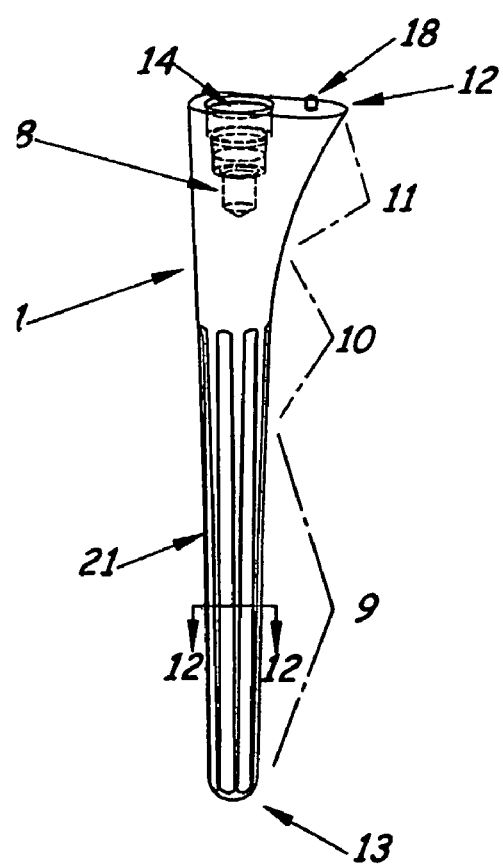
FIG. 11 is a view of a stem component of another exemplary embodiment of a joint prosthesis.
Figure 12:
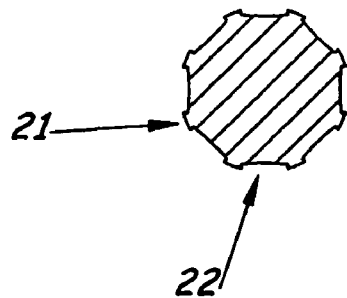
FIG. 12 is a cross section taken at the line 12-12 in FIG. 11.

FIGS. 4-12 illustrate various features of a number of alternative embodiments. FIG. 4 depicts a stem component 1 that has a rectangular cross section. The stem shown in FIG. 4 also tapers in the medial-lateral dimension but not in the anteroposterior direction. This can be seen in FIGS. 5 and 6, which are cross-sections of the stem shown in FIG. 4 taken at the cut lines indicated in the mid-shaft and distal shaft, respectively. FIG. 7 depicts an embodiment of a stem that includes grooves 19. The cross section shown in FIG. 8 shows the grooves more clearly. FIG. 9 shows a stem that defines a slot 20. FIG. 10 shows a cross-section of the distal stem and shows the exemplary slot more clearly. The slot divides the distal portion of the stem into tines. The stem may define slots at other angles and/or additional slots dividing the stem into several tines. Other tine configurations are described, for example, in U.S. Pat. No. 6,702,854 to Cheal et al., the entire contents of which are hereby incorporated herein by reference. FIG. 11 depicts an exemplary stem that includes ridges 21 and flutes 22. FIG. 12 shows a cross-section of the distal stem and depicts the ridges and flutes more clearly. FIG. 12 also depicts a roughly octagonal cross-sectional shape for the stem.

The invention claimed is:

1. A joint prosthesis comprising:
   a head member so sized and shaped as to be articulatable with a joint socket, the head member defining a head bore;
   a proximal body member that includes:
      a base;
      a plug protruding from the base and so sized and shaped as to be receivable in the head bore; and
      a spigot protruding from the base, the spigot including a locking band with a constant cross-sectional geometry along its length; and
   a stem member that includes:
      a proximal portion defining a stem bore that:
         is sized and shaped for receiving the spigot; and
         includes a receiving portion with a constant cross-sectional geometry along its length that is sized smaller than that of the locking band so that the locking band of the spigot engages the receiving portion by friction-tight press-fit as the proximal body member becomes fully seated on the stem member; and
      a shaft extending from the proximal portion, being sized and shaped for seating in a cavity of a long bone, and including:
         a midshaft portion of the stem member, at least a portion of which is so tapered that the cross-sectional area of the shaft in that portion continuously decreases distally; and
         a distal portion of the stem member, the distal portion terminating with a rounded distal tip.

2. The joint prosthesis of claim 1, wherein the locking band and the receiving portion are substantially cylindrical.

3. The joint prosthesis of claim 1, wherein the spigot of the proximal body member further includes a second locking band located further from the base of the proximal body than the first locking band, the second locking band having a constant cross-sectional geometry along the length of the second locking band, and a cross-sectional area that is smaller than the receiving portion of the stem bore for the first locking band.

4. The joint prosthesis of claim 3, wherein the bore of the stem member includes a receiving portion with a constant cross-sectional geometry that is equal to or smaller than that of the second locking band of the spigot of the proximal body member, for engaging the second locking band of the spigot as the proximal body member becomes fully seated on the stem member.

5. The joint prosthesis of claim 4, wherein the second locking band and the receiving portion for the second locking band are substantially cylindrical.

6. The joint prosthesis of claim 5, wherein both locking bands of the spigot of the proximal body member and both receiving portions of the bore of the stem member are substantially cylindrical.

7. The joint prosthesis of claim 6, wherein the locking bands of the spigot of the proximal body member are co-axial.

8. The joint prosthesis of claim 7, wherein:
the shaft is so tapered that the cross-sectional area of the shaft continuously decreases distally from the shaft's proximal end to distal end;
shaft tapers in a medial-lateral dimension but not in an antero-posterior dimension;
the midshaft tapered portion tapers linearly; and
the midshaft portion has a non-square rectangular cross section.

9. The joint prosthesis of claim 1, wherein the distal portion of the shaft of the stem member is generally round in cross-section.

10. The joint prosthesis of claim 1, wherein the proximal portion of the stem member is tapered in the medial-lateral dimension only.

11. The joint prosthesis of claim 1, wherein the proximal portion of the stem member is tapered in both the medial-lateral and the anterior-posterior directions.

12. The joint prosthesis of claim 1, wherein the base of the proximal body member defines at least one receptacle.

13. The joint prosthesis of claim 12, wherein the stem member further comprises a key protruding from the proximal end, the key so positioned as to be received in the at least one receptacle of the proximal body member as the stem bore receives the spigot.

14. The joint prosthesis of claim 13, wherein the base of the proximal body member further defines a plurality of receptacles, and the key is selectively positionable in one of the plurality of receptacles.

15. The joint prosthesis of claim 13, wherein the key of the stem member is substantially cylindrical.

16. The joint prosthesis of claim 13, wherein at least one receptacle of the proximal body member is substantially cylindrical.

17. The joint prosthesis of claim 13, wherein the key is located in the proximal body member and the plurality of receptacles are located in the stem member.

18. The joint prosthesis of claim 1, wherein the proximal body member defines a hole that passes through the spigot.

19. The joint prosthesis of claim 18, wherein the stem member defines a hole at the base of the bore.

20. The joint prosthesis of claim 19, wherein the hole of the stem member is so threaded as to receive a threaded bolt.

21. The joint prosthesis of claim 20, wherein the hole of the proximal body is coaxial to the hole of the stem member.

22. The joint prosthesis of claim 19, further comprising a bolt so passing through the hole of the proximal body and the hole of the stem member as to engage the stem member.

23. The joint prosthesis of claim 19, further comprising a bolt so passing through the hole of the proximal body and the hole of the stem member as to engage the stem member and the proximal body member.

24. The joint prosthesis of claim 1, wherein the entire midshaft portion of the shaft is so tapered that the cross-sectional area of the shaft continuously decreases distally throughout the midshaft portion.

25. The joint prosthesis of claim 24, wherein the entire midshaft and distal portions of the shaft are so tapered that the cross-sectional area of the shaft continuously decreases distally throughout the midshaft and distal portions.

26. The joint prosthesis of claim 1, wherein the shaft is so tapered that the cross-sectional area of the shaft continuously decreases distally from the shaft's proximal end to distal end.

27. The joint prosthesis of claim 26, wherein the shaft tapers in a medial-lateral dimension but not in an antero-posterior dimension.

28. The joint prosthesis of claim 1, wherein the distal portion of the shaft is so tapered that the cross-sectional area of the shaft in that portion continuously decreases distally.

29. The joint prosthesis of claim 1, wherein the midshaft tapered portion tapers linearly.

30. The joint prosthesis of claim 1, wherein the midshaft portion has a non-square rectangular cross section.

* * * * *